United States Patent [19]

Hofer et al.

[11] B  4,013,657

[45] Mar. 22, 1977

[54] O-ETHYL-S-n-PROPYL-O-[PYRIDAZ-(6)-ON-(3)-YL]-THIONOTHIOLPHOSPHORIC ACID ESTERS

[75] Inventors: Wolfgang Hofer; Fritz Maurer; Hans-Jochem Riebel; Lothar Rohe, all of Wuppertal; Ingeborg Hammann, Cologne; Wilhelm Stendel, Wuppertal, all of Germany

[73] Assignee: Bayer Aktiengesellschaft, Leverkusen, Germany

[22] Filed: Aug. 16, 1974

[21] Appl. No.: 498,288

[44] Published under the second Trial Voluntary Protest Program on March 23, 1976 as document No. B 498,288.

[30] Foreign Application Priority Data

Aug. 30, 1973 Germany .................. 2343741

[52] U.S. Cl. .................. 260/250 P; 71/87; 260/250 AP
[51] Int. Cl.$^2$ .................. C07F 9/40
[58] Field of Search .................. 260/250 AP, 250 P

[56] References Cited

UNITED STATES PATENTS

| 2,759,937 | 8/1956 | Du Breuil | 260/250 |
| 2,759,938 | 8/1956 | Du Breuil | 260/250 |
| 3,310,560 | 3/1967 | Schonbeck et al. | 260/250 |
| 3,547,920 | 12/1970 | Fest et al. | 260/250 |

Primary Examiner—R. J. Gallagher
Assistant Examiner—Mark L. Berch
Attorney, Agent, or Firm—Burgess, Dinklage & Sprung

[57] ABSTRACT

O-ethyl-S-n-propyl-O-[pyridaz-(6)-on-(3)-yl]-thionothiolphosphoric acid esters of the formula

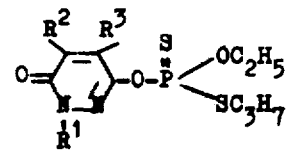

in which
R$^1$ is hydrogen, alkyl, substituted alkyl, alkenyl, alkynyl, aryl, substituted aryl, a five- or six-membered heterocyclic radical, or a five- or six-membered heterocyclic radical bonded to the nitrogen via a methyl group, and
R$^2$ and R$^3$ each independently is hydrogen or alkyl, or together are (CH)$_4$ forming a fused benzene ring with the adjoining carbon atoms which possess insecticidal and acaricidal properties.

6 Claims, No Drawings

O-ETHYL-S-n-PROPYL-O-[PYRIDAZ-(6)-ON-(3)-YL]-THIONOTHIOLPHOSPHORIC ACID ESTERS

The present invention relates to and has for its objects the provisions of particular new O-ethyl-S-n-propyl-O-[pyridaz-(6)-on-(3)-yl]-thionothiolphosphoric acid esters, which possess insecticidal or acaricidal properties, active compositions in the form of mixtures of such compounds with solid and liquid dispersible carrier vehicles, and methods for producing such compounds and for using such compounds in a new way especially for combating pests, e.g. insects and acarids, with other and further objects becoming apparent from a study of the within specification and accompanying examples.

It is known from U.S. Pat. Nos. 2,759,937, 2,759,938 and 3,310,560, and published Japanese patent application No. 20,025/72 that thionophosphoric acid esters, such as O,O-diethyl-O-[phthalaz-(8)-on-(3)-yl]- (Compound A), O,O-diethyl-O-[pyridaz-(6)-on-(3)-yl]- (Compound B), O,O-diethyl-O-[1-methyl-pyridaz-(6)-on-(3)-yl]- (Compound C), O,O-diethyl-O-[1-β-cyanoethyl-pyridaz-(6)-on-(3)-yl]- (Compound D), O,O-diethyl-O-[1-ethoxycarbonylmethyl-pyridaz-(6)-on-(3)-yl]- (Compound E) and O,O-diethyl-[1-p-methylphenyl-pyridaz-(6)-on-(3)-yl]-thionophosphoric acid esters (Compound F), possess good insecticidal and acaricidal properties. However, these compounds additionally have a high toxicity to warm-blooded animals.

The present invention provides, as new compounds, the O-ethyl-S-n-propyl-O-[pyridaz-(6)-on-(3)-yl]-thionothiolphosphoric acid esters of the formula

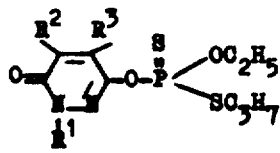

in which
R$^1$ is hydrogen, alkyl, substituted alkyl, alkenyl, alkynyl, aryl, substituted aryl, a five- or six-membered heterocyclic radical, or a five- or six-membered heterocyclic radical bonded to the nitrogen via a methyl group, and
R$^2$ and R$^3$ each independently is hydrogen or alkyl, or together are (CH)$_4$ forming a fused benzene ring with the adjoining carbon atoms.

Preferably, R$^1$ is hydrogen or straight-chain or branched alkyl with 1 to 6, especially 1 to 4, carbon atoms, which can carry one or more substituents selected from nitrile, halogen (especially chlorine and bromine), alkoxycarbonyl, alkylcarbonyl, alkoxy and alkylthio, in each case with 1 to 4, especially 1 to 3, carbon atoms in the alkyl moiety; a methyl group which is optionally substituted by a five-membered or six-membered, preferably completely hydrogenated, heterocyclic structure, which contains a hetero-atom, preferably N or S, or a hetero-group, preferably SO$_2$; alkenyl or alkynyl with 2 to 6, especially 2 to 4, carbon atoms; phenyl which can carry one or more substituents selected from halogen (such as chlorine, bromine or fluorine), alkyl with 1 to 4 carbon atoms (especially methyl and tert.-butyl), nitro, nitrile, alkoxy and alkylthio, each with 1 or 2 carbon atoms (for example ethoxy and methylthio), and halogenoalkyl with 1 or 2 carbon atoms and 2 to 5 halogen atoms (especially chlorine and/or fluorine atoms); or a 5-membered or 6-membered heterocyclic structure which contains a hetero-atom, preferably N or S, or a hetero-group, preferably NH or SO$_2$ (examples being thiophene-1,1-dioxide and piperidine); and
R$^2$ and R$^3$, independently of one another, are each hydrogen or straight-chain or branched alkyl with 1 to 4, especially 1 or 2, carbon atoms (for example, methyl and ethyl); or
R$^2$ and R$^3$ conjointly represent a methine bridge with four members which forms a fused benzene ring with the adjoining carbon atoms.

Surprisingly, the thionothiolphosphoric acid esters of the formula (I) exhibit a better insecticidal and acaricidal action, coupled with substantially lower toxicity to warm-blooded animals, than the prior-art compounds of analogous structure and of the same type of action. The active compounds according to the invention thus represent a genuine enrichment of the art.

Furthermore, the new compounds contribute to satisfying the continual demand for new preparations in the field of combating pests. This demand arises from the fact that the commercially available agents are required to meet over higher standards, particularly with regard to the protection of the environment, such as low toxicity to warm-blooded animals, low phytotoxicity, rapid degradation on and in the plant with minimum intervals to be observed between application of the pesticide and harvesting, activity against resistant pests, and the like.

The present invention also provides a process for the preparation of a thionothiolphosphoric acid ester of the formula (I), in which a maleic acid hydrazide derivative of the general formula

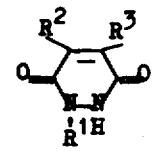

in which
R$^1$, R$^2$ and R$^3$ have the above-mentioned meanings, is reacted with an O-ethyl-S-propyl-thionothiolphosphoric acid ester halide of the general formula

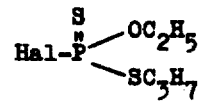

in which
Hal is a halogen atom, preferably a chlorine atom, optionally in the presence of a solvent or diluent and optionally in the presence of an acid-binding agent.

If, for example, maleic acid hydrazide and O-ethyl-S-n-propyl-thionothiolphosphoric acid ester chloride are used as starting compounds, the course of the reaction can be represented by the following equation:

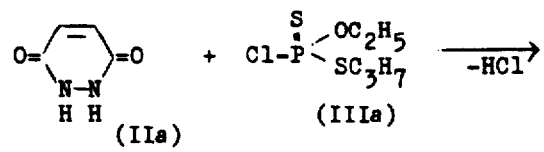

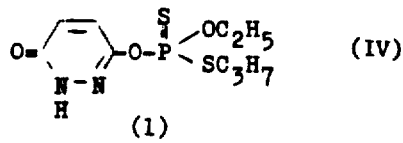

Maleic acid hydrazides of the formula (II) used as starting compounds are known from the literature and can be prepared according to customary methods.

The following may be mentioned as examples of maleic acid hydrazides which can be used as starting materials in accordance with the present process:

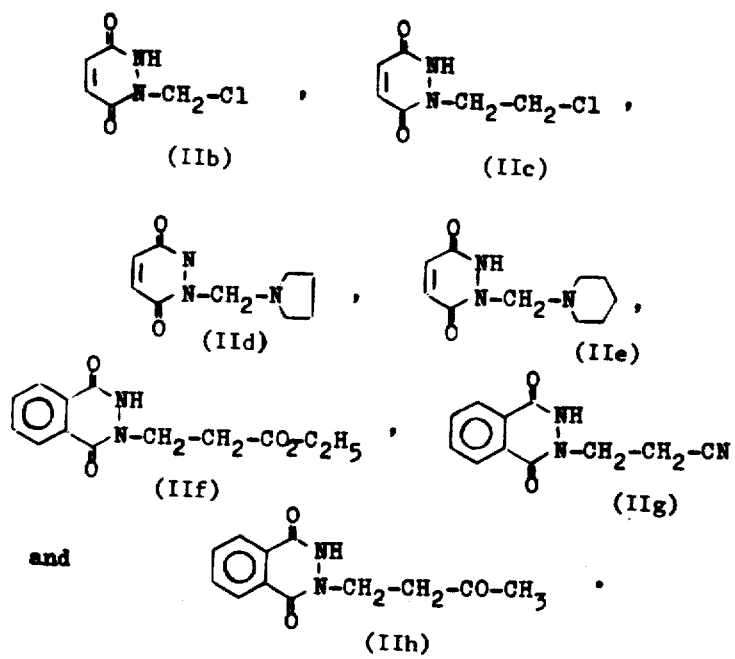

The phosphorylation process for the preparation of the new compounds (I) is preferably carried out with conjoint use of a suitable solvent or diluent. Practically all inert organic solvents can be used for this purpose, especially aliphatic and aromatic, optionally chlorinated, hydrocarbons, such as benzene, toluene, xylene, benzine, methylene chloride, chloroform, carbon tetrachloride and chlorobenzene; ethers, for example diethyl ether, dibutyl ether or dioxane; ketones, such as acetone, methyl ethyl ketone, methyl isopropyl ketone and methyl isobutyl ketone; nitriles, for example acetonitrile and propionitrile; and amides such as dimethylformamide and dimethylacetamide.

All customary acid-binding agents can be used as the acid acceptors. The following have proved particularly suitable: alkali metal carbonates and alkali metal alcoholates, such as sodium and potassium carbonate, methylate, ethylate and tert.-butylate, and also aliphatic, aromatic or heterocyclic amines, for example triethylamine, dimethylaniline, dimethylbenzylamine and pyridine.

The reaction temperatures can be varied within a fairly wide range. In general, the reaction is carried out at between −10° and +80°C, preferably at about 20° to 70°C.

The reaction is in general allowed to take place under normal pressure. To carry out the process, the starting compounds are generally employed in equimolar amounts. An excess of one or other reactant does not produce any significant advantages. The reaction is generally carried out in a suitable solvent in the presence of an acid acceptor and the reaction mixture is thereafter stirred for several hours. The mixture is then poured into water and worked up in accordance with customary methods. The new compounds are obtained in a crystalline form or as oils and can be characterized by their melting points and/or refractive indexes.

As has already been mentioned, the O-ethyl-S-n-propyl-O-[pyridaz-(6)-on-(3)-yl]-thionothiolphosphoric acid esters according to the invention are distinguished by an outstanding insecticidal and acaricidal activity both against plant pests and against pests harmful to health and pests of stored products. They have a good action against sucking and biting insects and against pests of the genus *Acarina*. For this reason, the compounds according to the invention may be employed successfully as pesticides in plant protection and in the hygiene field and veterinary field.

To the sucking insects there belong, in the main, aphids (*Aphididae*) such as the green peach aphid (*Myzus persicae*), the bean aphid (*Doralis fabae*), the bird cherry aphid (*Rhopalosiphum padi*), the pea aphid (*Macrosiphum pisi*) and the potato aphid (*Macrosiphum solanifolii*), the currant gall aphid (*Cryptomyzus korschelti*), the rosy apple aphid (*Sappaphis mali*), the mealy plum aphid (*Hyalopterus arundinis*) and the cherry black-fly (*Myzus cerasi*); in addition, scales and mealybugs (*Coccina*), for example the oleander scale (*Aspidiotus hederae*) and the soft scale (*Lecanium hesperidum*) as well as the grape mealybug (*Pseudococcus maritimus*); thrips (*Thysanoptera*), such as *Hercinothrips femoralis*, and bugs, for example the beet bug (*Piesma quadrata*), the red cotton bug (*Dysdercus intermedius*), the bed bug (*Cimex lectularius*), the assassin bug (*Rhodnius prolixus*) and Chagas' bug (*Triatoma infestans*) and, further, cicadas, such as *Euscelis bilobatus* and *Nephotettix bipunctatus*.

In the case of the biting insects, above all there should be mentioned butterfly caterpillars (*Lepidoptera*) such as the diamond-back moth (*Plutella maculipennis*), the gypsy moth (*Lymantria dispar*), the browntail moth (*Euproctis chrysorrhoea*) and tent caterpillar (*Malacosoma neustria*); further, the cabbage moth (*Mamestra brassicae*) and the cutworm (*Agrotis segetum*), the large white butterfly (*Pieris brassicae*), the small winter moth (*Cheimatobia brumata*), the green oak tortrix moth (*Tortrix viridana*), the fall armyworm (*Laphygma frugiperda*) and cotton worm (*Prodenia litura*), the ermine moth (*Hyponomeuta padella*), the Mediterranean flour moth (*Ephestia kuhniella*) and greater wax moth (*Galleria mellonella*).

Also to be classed with the biting insects are beetles (*Coleoptera*), for example the granary weevil (*Sitophilus granarius = Calandra granaria*), the Colorado beetle (*Leptinotarsa decemlineata*), the dock beetle (*Gastrophysa viridula*), the mustard beetle (*Phaedon cochleariae*), the blossom beetle (*Meligethes aeneus*), the raspberry beetle (*Byturus tomentosus*), the bean weevil (*Bruchidius = Acanthoscelides obtectus*), the leather beetle (*Dermestes frischi*), the khapra beetle (*Trogoderma granarium*), the flour beetle (*Tribolium castaneum*), the northern corn billbug (*Calandra* or *Sitophilus zeamais*), the drugstore beetle (*Stegobium paniceum*), the yellow mealworm (*Tenebrio molitor*) and the saw-toothed grain beetle (*Oryzaephilus surinamensis*), and also species living in the soil, for example wireworms (*Agriotes* spec.) and larvae of the cockchafer (*Melolontha melolontha*); cockroaches, such as the German cockroach (*Blattella germanica*), American cockroach (*Periplaneta americana*), Madeira cockroach (*Leucophaea* or *Rhyparobia maderae*), oriental cockroach (*Blatta orientalis*), the giant cockroach (*Blaberus giganteus*) and the black giant cockroach (*Blaberus fuscus*) as well as *Henschoutedenia flexivitta*; further *Orthoptera*, for example the house cricket (*Gryllus domesticus*); termites such as the eastern subterranean termite (*Reticulitermes flavipes*) and *Hymenoptera* such as ants, for example the garden ant (*Lasius niger*).

The *Diptera* comprise essentially the flies, such as the vinegar fly (*Drosophila melanogaster*), the Mediterranean fruit fly (*Ceratitis capitata*), the house fly (*Musca domestica*), the little house fly (*Fannia canicularis*), the black blow fly (*Phormia regina*) and bluebottle fly (*Calliphora erythrocephala*) as well as the stable fly (*Stomoxys calcitrans*); further, gnats, for example mosquitoes such as the yellow fever mosquito (*Aedes aegypti*), the northern house mosquito (*Culex pipiens*) and the malaria mosquito (*Anopheles stephensi*).

With the mites (*Acarina*) there are classed, in particular, the spider mites (*Tetranychidae*) such as the two-spotted spider mite (*Tetranychus urticae*) and the European red mite (*Paratetranychus pilosus = Panonychus ulmi*), gall mites, for example the blackcurrant gall mite (*Eriophyes ribis*) and tarsonemids, for example the broad mite (*Hemitarsonemus latus*) and the cyclamen mite (*Tarsonemus pallidus*); finally, ticks, such as the relapsing fever tick (*Ornithodorus moubata*).

In addition the active compounds according to the invention are distinguished by a very low toxicity to warm-blooded animals, which appears to make them outstandingly suitable for combating animal ectoparasites from the class of the insects, for example *Diptera* larvae which are parasitic in warm-blooded animals, such as *Lucilia sericata*, *Lucilia cuprina* (sensitive and resistant strains), *Chrysomyia chloropyga* and larvae of warble flies, for example the ox warble fly *Hypoderma bovis*.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other insecticides and acaricides, or rodenticides, fungicides, bactericides, nematocides, herbicides, fertilizers, growth-regulating agents, disinfectants, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates over-all compositions which comprise mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. insects and acarids, which comprises applying to at least one of correspondingly (a) such insects, (b) such acarids, and (c) the corresponding habitat thereof, i.e. the locus to be protected, e.g. to a growing crop, to an area where a crop is to be grown or to a domestic animal, a correspondingly combative or toxic amount, i.e. an insecticidally or acaricidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dressing or encrusting, or as a bath or dip as is usual in the field of veterinary medicine.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Drosophila test
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier, and the concentrate was diluted with water to the desired concentration.

1 ml of the preparation of the active compound was applied with a pipette to a filter paper disc of 7 cm diameter. The wet disc was placed over the orifice of a glass vessel containing 50 vinegar flies (*Drosophila melanogaster*) and covered with a glass plate.

After the specified periods of time, the destruction was determined in %. 100% means that all the flies were killed, and 0% means that no flies were killed.

The active compounds, the concentrations of the active compounds, the evaluation times and the degree of destruction can be seen from the following Table 1:

Table 1

| Active compound (*Drosophila* test) | | Active compound concentration in % | Degree of destruction in % after 1 day |
|---|---|---|---|
| (A) | (known) | 0.1 | 100 |
| | | 0.01 | 0 |
| | (3) | 0.1 | 100 |
| | | 0.01 | 100 |

Table 1-continued
(Drosophila test)

| Active compound | Active compound concentration in % | Degree of destruction in % after 1 day |
|---|---|---|
| 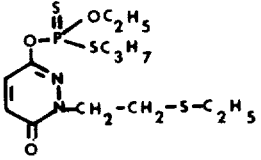 (8) | 0.1<br>0.01 | 100<br>100 |
| 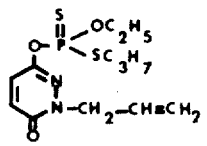 (6) | 0.1<br>0.01 | 100<br>100 |
| 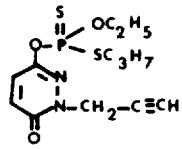 (7) | 0.1<br>0.01 | 100<br>100 |
| 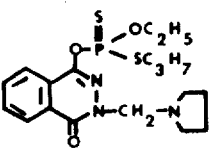 (19) | 0.1<br>0.01 | 100<br>100 |
| 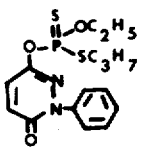 (13) | 0.1<br>0.01 | 100<br>100 |

EXAMPLE 2

Plutella test
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (Brassica oleracea) were sprayed with the preparation of the active compound until dew moist and were then infested with caterpillars of the diamond-back moth (*Plutella maculipennis*).

After the specified periods of time, the degree of destruction was determined as a percentage: 100% means that all the caterpillars were killed, whereas 0% means that none of the caterpillars were killed.

The active compounds, the concentrations of the active compounds, the evaluation times and the results can be seen from the following Table 2.

Table 2

(*Plutella* test)

| Active compound | Active compound concentration in % | Degree of destruction in % after 3 days |
|---|---|---|

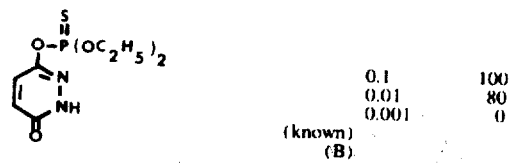

| (known) (B) | 0.1 | 100 |
| | 0.01 | 80 |
| | 0.001 | 0 |

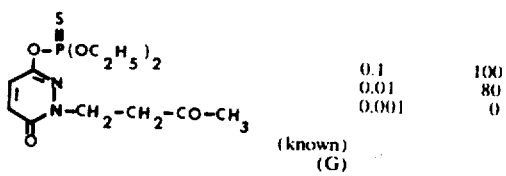

| (known) (G) | 0.1 | 100 |
| | 0.01 | 80 |
| | 0.001 | 0 |

| (known) (A) | 0.1 | 0 |

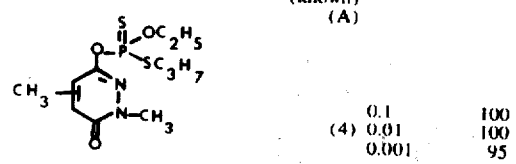

| (4) | 0.1 | 100 |
| | 0.01 | 100 |
| | 0.001 | 95 |

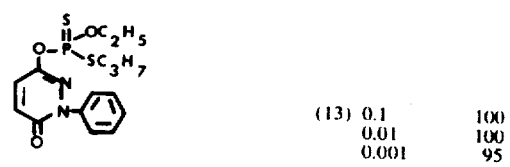

| (13) | 0.1 | 100 |
| | 0.01 | 100 |
| | 0.001 | 95 |

| (14) | 0.1 | 100 |
| | 0.01 | 100 |
| | 0.001 | 95 |

Table 2-continued

| (*Plutella* test) Active compound | Active compound concentration in % | Degree of destruction in % after 3 days |
|---|---|---|
| 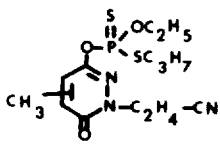 (12) | 0.1 0.01 0.001 | 100 100 100 |

EXAMPLE 3

Tetranychus test (resistant)
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Bean plants (*Phaseolus vulgaris*), which had a height of approximately 10–30 cm, were sprayed with the preparation of the active compound until dripping wet. These bean plants were heavily infested with the two-spotted spider mite (*Tetranychus urticae*) in all stages of development.

After the specified periods of time, the effectiveness of the preparation of active compound was determined by counting the dead mites. The degree of destruction thus obtained was expressed as a percentage: 100% means that all the spider mites were killed whereas 0% means that none of the spider mites were killed.

The active compounds, the concentrations of the active compounds, the evaluation times and the results can be seen from the following Table 3:

Table 3

| (*Tetranychus* test) Active compound | Active compound concentration in % | Degree of destruction in % after 2 days |
|---|---|---|
| 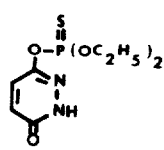 (known) (B) | 0.1 | 20 |
| 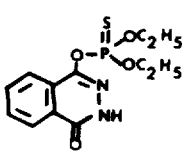 (known) (A) | 0.1 | 0 |
| 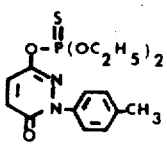 (known) (F) | 0.1 0.01 | 40 0 |

Table 3-continued (*Tetranychus* test)

| Active compound | Active compound concentration in % | Degree of destruction in % after 2 days |
|---|---|---|
| (3) | 0.1<br>0.01 | 100<br>70 |
| (8) | 0.1<br>0.01 | 100<br>80 |
| (6) | 0.1<br>0.01 | 100<br>55 |
| (7) | 0.1<br>0.01 | 100<br>45 |
| (20) | 0.1<br>0.01 | 100<br>80 |
| (13) | 0.1<br>0.01 | 100<br>100 |

EXAMPLE 4

Test with parasitic fly larvae
Solvent:
    35 parts by weight of ethylene polyglycol monomethyl ether
    35 parts by weight of nonylphenol polyglycol ether To produce a suitable preparation of active compound, 30 parts by weight of the active substance in question were mixed with the stated amount of solvent which contained the above-mentioned proportion of emulsifier and the concentrate thus obtained was diluted with water to the desired concentration.

About 20 fly larvae (*Lucilia cuprina*) were introduced into a test tube which contained approximately 2 ml of horse muscle. 0.5 ml of the preparation of active compound was applied to this horse meat. After 24 hours, the degree of destruction in % was determined. 100% means that all the larvae had been killed and 0% means that no larvae had been killed. The test results obtained are listed in Table 4.

Evaluation after: 7 days

To produce a suitable preparation of active compound, 3 parts by weight of active compound were mixed with 2.8 parts by weight of highly disperse silica and 4.2 parts by weight of talc. Suspensions, which contained, in 1 ml of liquid, the amount of active compound to be adminstered per 100 g of animal weight, were prepared from the above active-compound concentrate, with addition of a little powdered vegetable gum, by trituration with water. The dosage was measured out volumetrically after weighing the test animals. It was administered orally by means of a steel Table 4

| (Test with parasitic fly larvae/*Lucilia cuprina* res.) Active compound | | Active compound concentration in ppm | Degree of destruction in % |
|---|---|---|---|
| 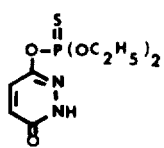 (known) (B) | | 300<br>30 | 100<br><50 |
| 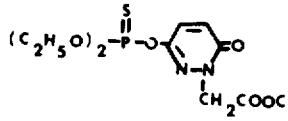 (known) (E) | | 100<br>10 | 100<br>>50 |
| 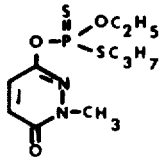 | (3) | 100<br>30<br>10 | 100<br>100<br>100 |
| 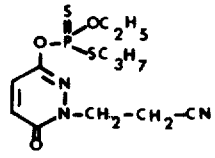 | (2) | 100<br>30<br>10 | 100<br>100<br>100 |
| 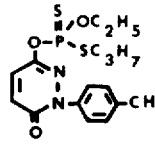 | (15) | 100<br>30<br>10<br>3 | 100<br>100<br>100<br>>50 |

EXAMPLE 5

Toxicity test/peroral
Test animal: Albino rat (*Rattus norvegicus*)

knob-ended probe. The results were in each case evaluated at the end of the above-mentioned interval of time, calculated from the administration of the active compound.

The LD₅₀ values (dose of active compound which kills 50% of the treated animals) was determined from the mortality values of the dose which were varied in geometrical progression, in the usual manner.

The active compounds and LD₅₀ values can be seen from Table 5 which follows.

Table 5

| (Toxicity test, albino rat/*peroral*) Active compound | LD₅₀ value (in mg/kg of body weight) |
|---|---|
| 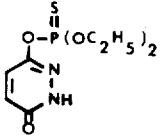 (known) (B) | 2.5–5 |
| 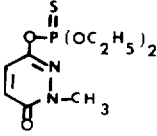 (known) (C) | 5–10 |
| 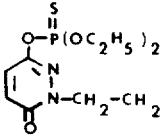 (known) (D) | 10–25 |
| 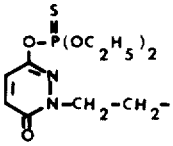 (known) (G) | 10–25 |
| 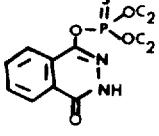 (known) (A) | approx. 25 |
| 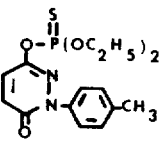 (known) (F) | 50–100 |

Table 5-continued
(Toxicity test, albino rat/peroral)
| Active compound | | LD$_{50}$ value (in mg/kg of body weight) |
|---|---|---|
| 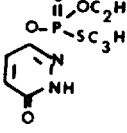 | (1) | 100 – 250 |
| 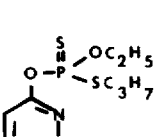 | (3) | 100 – 250 |
| 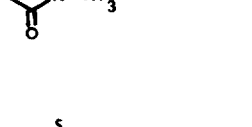 | (8) | 250 – 500 |
| 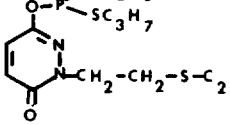 | (9) | approx. 500 |
| 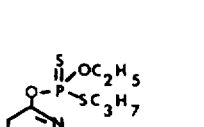 | (6) | approx. 500 |
| 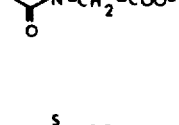 | (7) | approx. 250 |
| 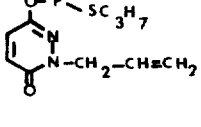 | (2) | 250 – 500 |

Table 5-continued
| (Toxicity test, albino rat/peroral) Active compound | | LD$_{50}$ value (in mg/kg of body weight) |
|---|---|---|
| 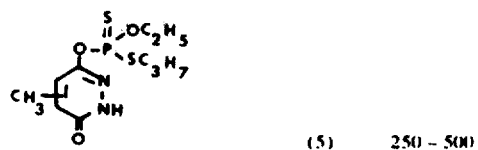 | (5) | 250 – 500 |
| 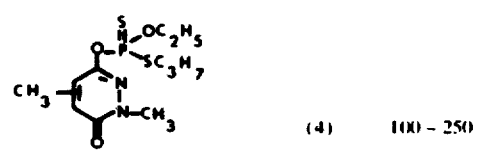 | (4) | 100 – 250 |
| 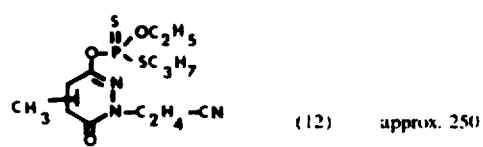 | (12) | approx. 250 |
| 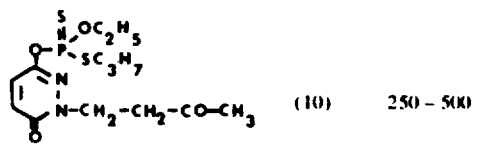 | (10) | 250 – 500 |
| 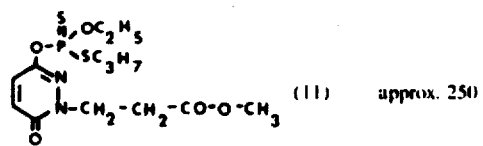 | (11) | approx. 250 |
| 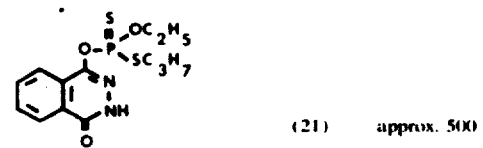 | (21) | approx. 500 |
| 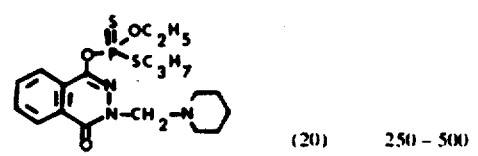 | (20) | 250 – 500 |

Table 5-continued
| Active compound (Toxicity test, albino rat/peroral) | | LD$_{50}$ value (in mg/kg of body weight) |
|---|---|---|
| 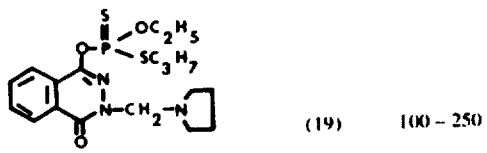 | (19) | 100 – 250 |
|  | (18) | approx. 500 |
| 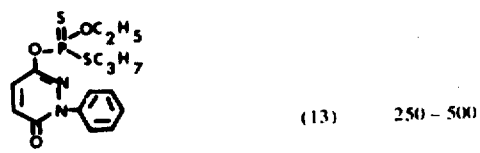 | (13) | 250 – 500 |
| 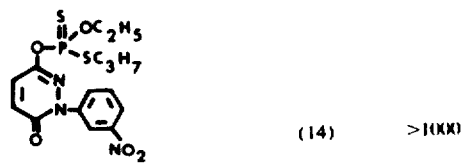 | (14) | >1000 |
| 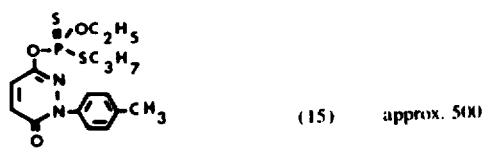 | (15) | approx. 500 |
| 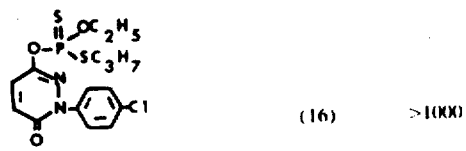 | (16) | >1000 |

Table 5-continued (Toxicity test, albino rat/peroral)

| Active compound | | LD$_{50}$ value (in mg/kg of body weight) |
|---|---|---|
| 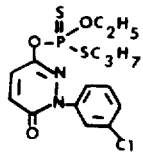 | (17) | >1000 |

The process of the present invention is illustrated in the following preparative Examples.

EXAMPLE 6

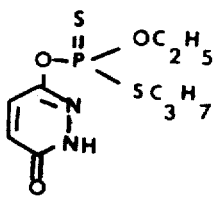

(1)

65.6 g (0.3 mole) of O-ethyl-S-n-propyl-thionothiolphosphoric acid ester chloride were added to a suspension of 33.6 g (0.3 mole) of maleic acid hydrazide and 31.8 g (0.3 mole) of sodium carbonate in 500 ml of dimethylformamide. The mixture was then stirred for 24 hours at room temperature, the resulting sodium chloride was filtered off and the resulting solution was freed from the solvent under reduced pressure. The residue was taken up in toluene, the solution was washed with 10 percent strength sodium carbonate solution and then with water, the organic phase was dried over sodium sulfate and then again freed from the solvent under reduced pressure. The residue was dissolved in a little ether and the product was precipitated with heptane.

46 g (51% of theory) of O-ethyl-S-n-propyl-O-[pyridaz-(6)-on-(3)-yl]-thionothiolphosphoric acid ester of melting point 56°C were obtained.

EXAMPLE 7

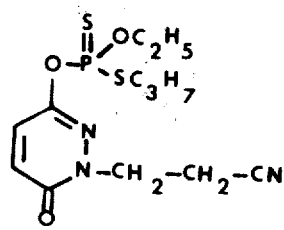

(2)

21.8 g (0.1 mole) of O-ethyl-S-n-propyl-thionothiolphosphoric acid ester chloride were added to a mixture of 16.5 g (0.1 mole) of 1,6-dihydro-1-cyanoethyl-3-hydroxy-6-oxopyridazine, 14.5 g (0.105 mole) of potassium carbonate and 200 ml of acetonitrile. The reaction mixture was warmed to 40°C for 3 hours and was then cooled and poured into 300 ml of toluene. The batch was washed with saturated sodium bicarbonate solution and with water and after drying over sodium sulfate the solvent was distilled off under reduced pressure.

23 g (66% of theory) of O-ethyl-S-n-propyl-O-[1-β-cyanoethyl-pyridaz-(6)-on-(3)-yl]-thionothiolphosphoric acid ester were obtained as a yellow oil of refractive index $n_D^{22}$ of 1.5523.

The compounds listed in Table 6 which follows were obtained by the methods described above.

Table 6

| Compound No. | R$^1$ | R$^2$ | R$^3$ | Melting point °C, or refractive index |
|---|---|---|---|---|
| 3 | CH$_3$ | H | H | $n_D^{25}$ 1.5376 |
| 4 | CH$_3$ | CH$_3$ | H | |
| | | H (isomer mixture) | CH$_3$ | $n_D^{23}$ 1.5489 |
| 5 | H | CH$_3$ | H | |
| | | H (isomer mixture) | CH$_3$ | $n_D^{21}$ 1.5588 |

Table 6-continued

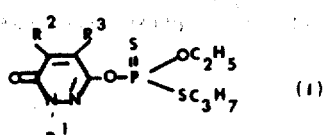

(1)

| Compound No. | R¹ | R² | R³ | Melting point °C, or refractive index |
|---|---|---|---|---|
| 6 | CH₂—CH=CH₂ | H | H | $n_D^{25}$ 1.5475 |
| 7 | CH₂—CH CH | H | H | $n_D^{25}$ 1.5203 |
| 8 | C₂H₄—SC₂H₅ | H | H | $n_D^{25}$ 1.5372 |
| 9 | CH₂COOC₂H₅ | H | H | $n_D^{25}$ 1.5353 |
| 10 | C₂H₄COCH₃ | H | H | $n_D^{22}$ 1.5563 |
| 11 | C₂H₄COOCH₃ | H | H | $n_D^{25}$ 1.5430 |
| 12 | C₂H₄CN | H | CH₃ | |
| | | CH₃ (isomer mixture) | H | $n_D^{25}$ 1.4465 |
| 13 | —⟨phenyl⟩ | H | H | $n_D^{25}$ 1.5420 |
| 14 | —⟨phenyl-NO₂⟩ | H | H | $n_D^{25}$ 1.6015 |
| 15 | —⟨phenyl-CH₃⟩ | H | H | $n_D^{25}$ 1.5706 |
| 16 | —⟨phenyl-Cl⟩ | H | H | $n_D^{25}$ 1.5950 |
| 17 | —⟨phenyl-Cl⟩ | H | H | $n_D^{20}$ 1.5998 |
| 18 | O₂S-ring | H | H | 60 |
| 19 | -CH₂-N⟨piperidyl⟩ | H | ⟨phenyl⟩ | $n_D^{25}$ 1.5738 |
| 20 | -CH₂-N⟨piperidyl⟩ | H | ⟨phenyl⟩ | $n_D^{25}$ 1.5783 |
| 21 | H | H | ⟨phenyl⟩ | 75 |
| 22 | C₂H₄CN | H | ⟨phenyl⟩ | $n_D^{22}$ 1.5773 |
| 23 | C₂H₄COCH₃ | H | ⟨phenyl⟩ | $n_D^{22}$ 1.5790 |
| 24 | C₂H₄COOC₂H₅ | H | ⟨phenyl⟩ | $n_D^{25}$ 1.5645 |

It will be appreciated that the instant specification and examples are set forth by way of illustration and not limitation, and that various modifications and changes may be made without departing from the spirit and scope of the present invention.

Whaat is claimed is:

1. An O-ethyl-S-n-propyl-O-[pyridaz-(6)-on-(3)-yl]-thiono-thiolphosphoric acid ester of the formula

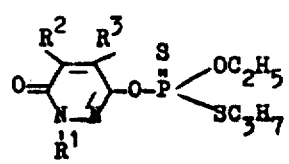

in which

R¹ is hydrogen, alkyl with 1 to 6 carbon atoms, or alkyl with 1 to 6 carbon atoms carrying a substituent selected from nitrile, halogen, alkoxycarbonyl, alkylcarbonyl, alkoxy and alkylthio, in each case with 1 to 4 carbon atoms in the alkyl moiety; methyl substituted by pyrrolidine, piperidine or thiophene-1,1-dioxide; alkenyl or alkynyl with 2 to 6 carbon atoms; phenyl or phenyl carrying one substituent selected from halogen, alkyl with 1 to 4 carbon atoms, nitro, nitrile, alkoxy and alkylthio, each with 1 or 2 carbon atoms and 2 to 5 halogen atoms; pyrrolidine, piperidine or thiophene-1,1-dioxide, and R² and R³ each independently is hydrogen or alkyl with 1 to 4 carbon atoms, or together are (CH)₄ forming a fused benzene ring with the adjoining carbon atoms.

2. The compound according to claim 1 wherein such compound is at least one of O-ethyl-S-n-propyl-O-[1-methyl-4- and 5-methyl-pyridaz-(6)-on-(3)-yl]-thionothiolphosphoric acid esters of the formulas

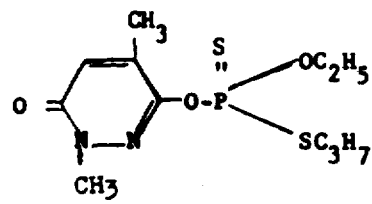 and 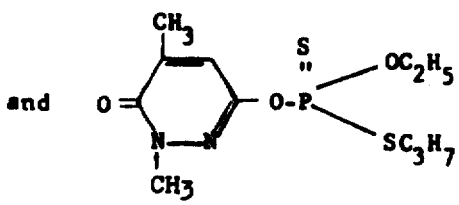

3. The compound according to claim 1 wherein such compound is O-ethyl-S-n-propyl-O-[1-ethoxycarbonyl-methyl-pyridaz-(6)-on-(3)-yl]-thionothiolphosphoric acid ester of the formula

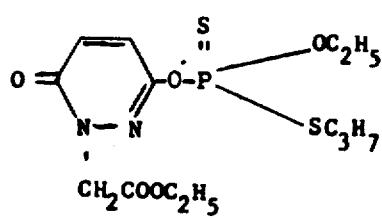

4. The compound according to claim 1 wherein such compound is at least one of O-ethyl-S-n-propyl-O-[1-β-cyanoethyl-4- and 5-methyl-pyridaz-(6)-on-(3)-yl]-thionothiolphosphoric acid esters of the formulas

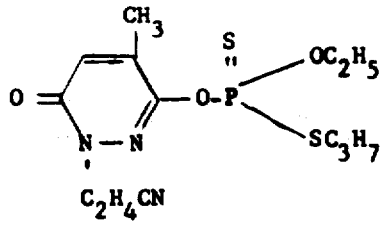 and 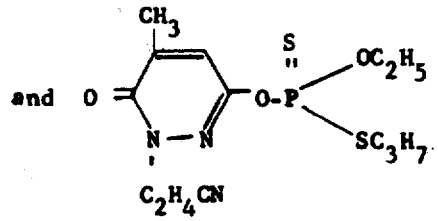

5. The compound according to claim 1 wherein such compound is O-ethyl-S-n-propyl-O-[1-phenyl-pyridaz-(6)-on-(3)-yl]-thionothiolphosphoric acid ester of the formula

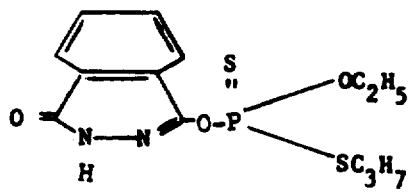

6. The compound according to claim 1 wherein such compound is O-ethyl-S-n-propyl-O-[phthalaz-(8)-on-(3)-yl]-thionothiolphosphoric acid ester of the formula

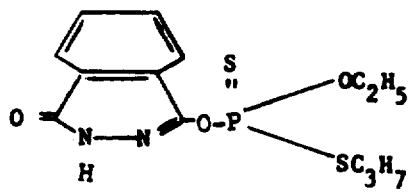

* * * * *